US012702703B2

(12) United States Patent
Zhang

(10) Patent No.: US 12,702,703 B2
(45) **Date of Patent: *Aug. 11, 2026**

(54) EDIBLE PLANT EXOSOME-LIKE NANOVECTORS FOR VACCINATION

(71) Applicant: University of Louisville Research Foundation, Inc., Louisville, KY (US)

(72) Inventor: Huang-Ge Zhang, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/889,715

(22) Filed: Aug. 17, 2022

(65) Prior Publication Data

US 2023/0210971 A1 Jul. 6, 2023

Related U.S. Application Data

(63) Continuation of application No. 17/050,200, filed as application No. PCT/US2019/029377 on Apr. 26, 2019, now abandoned.

(60) Provisional application No. 62/663,016, filed on Apr. 26, 2018.

(51) Int. Cl.

| | |
|---|---|
| ***A61K 39/00*** | (2006.01) |
| ***A61K 9/00*** | (2006.01) |
| ***A61K 9/1277*** | (2025.01) |
| ***A61K 31/05*** | (2006.01) |
| ***A61K 31/12*** | (2006.01) |
| ***A61K 31/203*** | (2006.01) |
| ***A61K 31/337*** | (2006.01) |
| ***A61K 31/353*** | (2006.01) |
| ***A61K 31/475*** | (2006.01) |
| ***A61K 31/513*** | (2006.01) |
| ***A61K 31/704*** | (2006.01) |
| ***A61K 33/243*** | (2019.01) |
| ***A61K 38/12*** | (2006.01) |
| ***A61K 39/39*** | (2006.01) |
| ***A61P 35/00*** | (2006.01) |
| ***A61P 35/04*** | (2006.01) |
| ***C12N 15/113*** | (2010.01) |

(52) U.S. Cl.

CPC ........ *A61K 39/0012* (2013.01); *A61K 9/0056* (2013.01); *A61K 9/1277* (2013.01); *A61K 31/05* (2013.01); *A61K 31/12* (2013.01); *A61K 31/203* (2013.01); *A61K 31/337* (2013.01); *A61K 31/353* (2013.01); *A61K 31/475* (2013.01); *A61K 31/513* (2013.01); *A61K 31/704* (2013.01); *A61K 33/243* (2019.01); *A61K 38/12* (2013.01); *A61K 39/0011* (2013.01); *A61K 39/001102* (2018.08); *A61K 39/39* (2013.01); *A61P 35/00* (2018.01); *A61P 35/04* (2018.01); *C12N 15/1135* (2013.01); *A61K 2039/55* (2013.01); *A61K 2039/6018* (2013.01); *A61K 2039/812* (2018.08); *C12N 2310/14* (2013.01); *C12N 2310/141* (2013.01); *C12N 2310/531* (2013.01)

(58) Field of Classification Search

CPC .............. A61K 39/0012; A61K 9/0056; A61K 9/1277; A61K 31/05; A61K 31/12; A61K 31/203; A61K 31/337; A61K 31/353; A61K 31/475; A61K 31/513; A61K 31/704; A61K 33/243; A61K 38/12; A61K 39/001102; A61K 39/39; A61K 2039/55; A61K 2039/6018; A61K 2039/812; A61K 39/0011; A61K 2039/542; A61K 2039/55555; A61K 2039/876; A61P 35/00; A61P 35/04; C12N 15/1135; C12N 2310/14; C12N 2310/141; C12N 2310/531; C12N 15/111; C12N 2320/32

See application file for complete search history.

(56) References Cited

U.S. PATENT DOCUMENTS

| | | | | |
|---|---|---|---|---|
| 11,111,488 B2 * | 9/2021 | Viola | ................. | C12N 15/1006 |
| 2016/0354313 A1 * | 12/2016 | De Beer | .............. | A61K 9/1271 |
| 2018/0177816 A1 * | 6/2018 | Shiku | ..................... | A61K 35/17 |

FOREIGN PATENT DOCUMENTS

| | | | |
|---|---|---|---|
| WO | WO-2011097480 A1 * | 8/2011 | ............. A61K 31/05 |
| WO | WO-2013048734 A1 * | 4/2013 | ........... A61L 31/047 |
| WO | WO-2017004526 A1 * | 1/2017 | ......... A61K 31/7088 |

OTHER PUBLICATIONS

Humphreys et al.,.PLOS ONE, 2014, 9(1 1):e 112288. (Year: 2014).*

* cited by examiner

*Primary Examiner* — Robert S Cabral

(74) *Attorney, Agent, or Firm* — Meunier Carlin & Curfman LLC

(57) ABSTRACT

Provided are compositions and methods for using the same. In some embodiments, the compositions include an EPELN encapsulating and/or having associated therewith an active agent and a plasma membrane derived from a tumor and/or cancer cell coating the EPELN. In some embodiments, the active agent is a therapeutic agent or an immune response modifier, and in some embodiments the plasma membrane has one or more tumor-associated and/or cancer-associated antigens. Also provided are methods for using the compositions for treating tumors and/or cancers, inducing anti-tumor and/or anti-cancer immune responses, activating antigen-presenting cells, targeting CD11c dendritic cells, and preventing or reducing metastasis.

22 Claims, 5 Drawing Sheets

Figure 1:
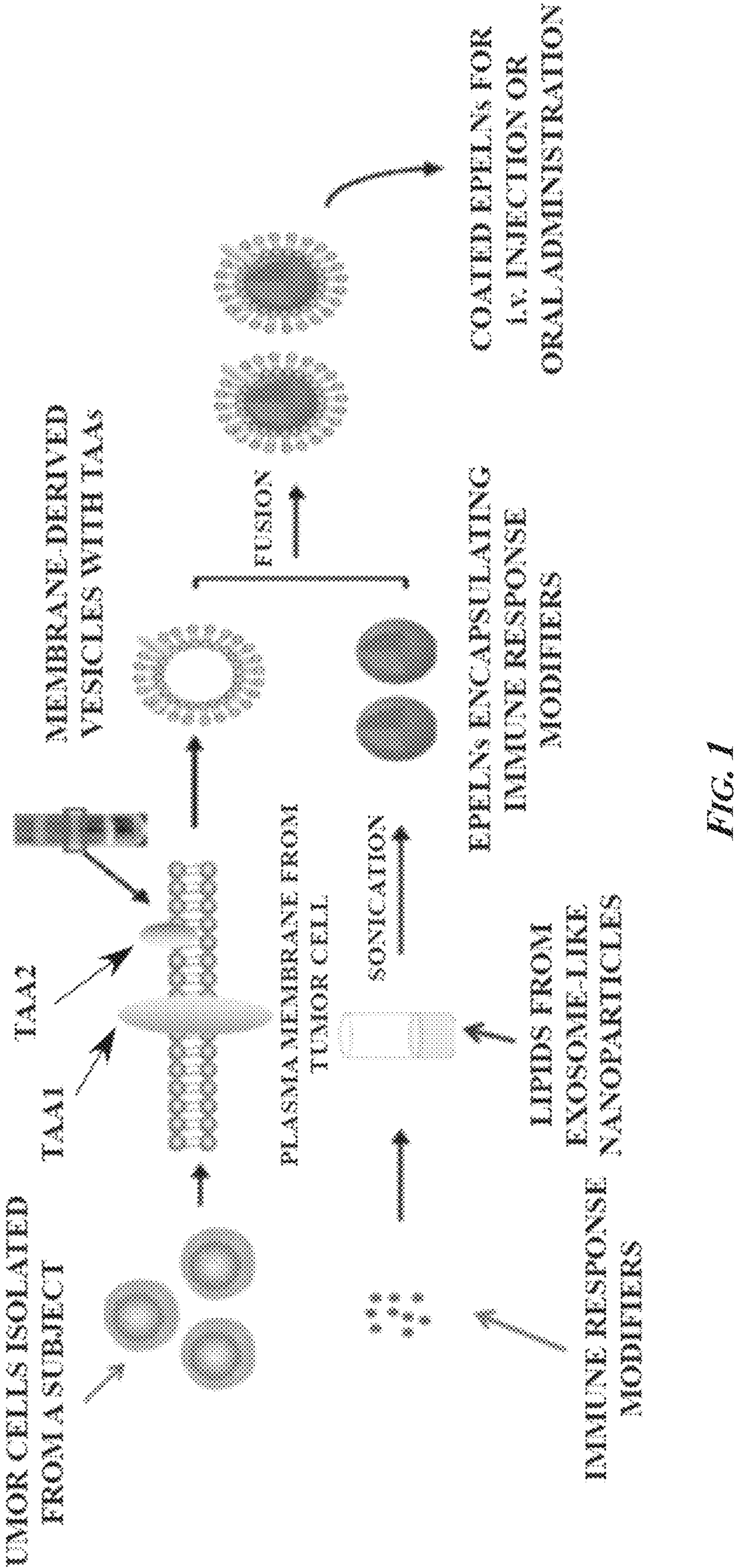

Specification includes a Sequence Listing.

EDIBLE PLANT EXOSOME-LIKE NANOVECTORS FOR VACCINATION

CROSS REFERENCE TO RELATED APPLICATION

This application is a continuation of U.S. patent application Ser. No. 17/050,200, filed Oct. 23, 2020, which is a United States National Stage application of PCT/US2019/029377, filed Apr. 26, 2019, itself claimed priority from U.S. Provisional Application Ser. No. 62/663,016, filed Apr. 26, 2018, the entire disclosure of which is incorporated herein by this reference.

GOVERNMENT INTEREST

This invention was made with government support under TR00875 and R01 AT008617 awarded by the National Institutes of Health. The government has certain rights in the invention.

REFERENCE TO SEQUENCE LISTING XML

The Sequence Listing XML associated with the instant disclosure has been electronically submitted to the United States Patent and Trademark Office via the Patent Center as a 2,704 byte UTF-8-encoded XML file created on Aug. 16, 2022 and entitled "1577_53_2_PCT_US_CON.xml". The Sequence Listing submitted via Patent Center is hereby incorporated by reference in its entirety.

TECHNICAL FIELD

The presently disclosed subject matter generally relates to edible plant exosome-like nanovectors (EPELN). In particular, certain embodiments of the presently disclosed subject matter relate to edible plant exosome-like nanovectors that include exosome-like nanoparticles coated with plasma membranes derived from a tumor cell.

BACKGROUND

Nanotechnology relates to the application of nanoscale or nanostructured material to medicine, particularly with respect to delivery of therapeutic molecules to cells and tissues of interest. Nanoparticles with sizes of up to 1000 nm and made from various materials, such as polymers, liposomes, metals, and carbon nanotubes, are potential therapeutic agent delivery vectors. Compositions and methods by which small molecule drugs, peptides, proteins, DNA, and even siRNA molecules are packed into nanoparticles and then used to treat multiple fungal infections, inflammatory diseases, bone defects, and cancers have been developed and/or are current objectives of many medical research efforts.

Despite ongoing research into the use of nanoparticles as therapeutic agent-delivery vectors, however, in the fight against tumors and cancers, localized drug delivery and specific targeting to tumor and/or cancer cells remain difficult. Indeed, one of the most challenging issues in anti-tumor and anti-cancer therapy continues to be achieving delivery of therapeutic agents to specific tumor and/or cancer cells in vivo, particularly with the therapeutic agent retaining its therapeutic activity upon delivery.

Recently, efforts have been made to confront these problems via the further development of nanoparticle-therapeutic agent delivery systems to enhance host immune system against cancer. To date, however, the development of an efficient and specific nanoparticle-therapeutic agent delivery system that is able to deliver therapeutic agents to tumor and cancer cells and immune cells, in particular antigen presenting cells while retaining sufficient biological activity of any payload that might be carried remains elusive.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides compositions comprising an edible-plant derived exosome-like nanoparticle (EPELN) encapsulating and/or having associated therewith an active agent selected from the group consisting of a therapeutic agent and an immune response modifier; and a plasma membrane derived from a tumor and/or cancer cell coating the EPELN, wherein the plasma membrane comprises one or more tumor-associated and/or cancer-associated antigens. In some embodiments, the immune response modifier comprises an miRNA, optionally wherein the miRNA is selected from the group consisting of miR18a (5'-UAAGGUGCAUCUAGUGCAGAUAG-3'; SEQ ID NO: 1) and miR17 (5'-CAAAGUGCUUACAGUGCAGGUAG-3'; SEQ ID NO: 2). In some embodiments, the plasma membrane comprises one or more tumor-associated antigens. In some embodiments, the edible plant is a mushroom. In some embodiments, the therapeutic agent is selected from a phytochemical agent, an immune-response inducing and/or enhancing agent, and a chemotherapeutic agent. In some embodiments, the therapeutic agent is a phytochemical agent, optionally wherein the phytochemical agent is selected from curcumin, resveratrol, baicalein, equol, fisetin, and quercetin. In some embodiments, the therapeutic agent is a chemotherapeutic agent, optionally wherein the chemotherapeutic agent is selected from the group consisting of retinoic acid, 5-fluorouracil, vincristine, actinomycin D, adriamycin, cisplatin, docetaxel, doxorubicin, and taxol. In some embodiments, the therapeutic agent comprises a nucleic acid molecule selected from the group consisting of an siRNA, a microRNA, and a mammalian expression vector.

In some embodiments, the presently disclosed subject matter also provides pharmaceutical compositions comprising a pharmaceutically-acceptable vehicle, carrier, and/or excipient and a composition comprising an edible-plant derived exosome-like nanoparticle (EPELN) encapsulating and/or having associated therewith an active agent selected from the group consisting of a therapeutic agent and an immune response modifier; and a plasma membrane derived from a tumor and/or cancer cell coating the EPELN, wherein the plasma membrane comprises one or more tumor-associated and/or cancer-associated antigens. In some embodiments, the pharmaceutical composition is pharmaceutically acceptable for use in a human.

In some embodiments, the presently disclosed subject matter also provides methods for treating tumors and/or cancers. In some embodiments, the methods comprise administering to a subject in need thereof an effective amount of a composition, the composition comprising an edible-plant derived exosome-like nanoparticle (EPELN) encapsulating and/or having associated therewith an active agent selected from the group consisting of a therapeutic agent and an immune response modifier; and a plasma membrane derived from a tumor and/or cancer cell coating the EPELN, wherein the plasma membrane comprises one or more tumor-associated and/or cancer-associated antigens. In some embodiments, the methods comprise providing an edible-plant derived exosome-like nanoparticle (EPELN) encapsulating and/or having associated therewith an active agent selected from the group consisting of a therapeutic agent and an immune response modifier; coating the EPELN with a plasma membrane derived from a tumor and/or a cancer cell isolated from the subject to produce a therapeutic composition; and administering an effective amount of the therapeutic composition to the subject, whereby the therapeutic composition induces an immune response in the subject against a tumor-associated and/or cancer-associated antigen to thereby treat the tumor and/or the cancer in the subject. In some embodiments, the tumor cell and/or cancer cell is autologous to the subject.

In some embodiments, the presently disclosed subject matter also provides methods for inducing an anti-tumor and/or an anti-cancer immune response in a subject. In some embodiments, the methods comprise administering to the subject an effective amount of a composition as disclosed herein, whereby an anti-tumor and/or anti-cancer immune response is induced in the subject to at least one tumor-associated and/or cancer-associated antigen present in the composition.

In some embodiments, the presently disclosed subject matter also provides methods for activating antigen-presenting cells (APCs) in a subject. In some embodiments, the methods comprise administering to the subject an effective amount of the composition as disclosed herein, whereby APCs present in the subject are activated against at least one tumor-associated and/or cancer-associated antigen present in the subject.

In some embodiments, the presently disclosed subject matter also provides methods for activating an antigen-presenting cell (APC) in a subject against a tumor cell and/or a cancer cell. In some embodiments, the methods comprise administering to the subject an effective amount of a composition comprising an edible-plant derived exosome-like nanoparticle (EPELN) encapsulating and/or having associated therewith an active agent selected from the group consisting of a therapeutic agent and an immune response modifier; and a plasma membrane derived from a tumor and/or cancer cell coating the EPELN, wherein the plasma membrane comprises one or more tumor-associated and/or cancer-associated antigens, whereby an antigen-presenting cell (APC) in a subject is activated against the tumor cell and/or the cancer cell.

In some embodiments, the presently disclosed subject matter also provides methods for targeting CD11c dendritic cells present in or isolated from a subject. In some embodiments, the methods comprise contacting the CD11c dendritic cell with a composition as disclosed herein.

In some embodiments, the presently disclosed subject matter also provides methods for preventing or reducing metastasis of a cancer in a subject in need thereof. In some embodiments, the methods comprise administering to the subject an effective amount of a composition as disclosed herein.

In some embodiments of the presently disclosed methods, the composition is administered orally or intravenously.

In some embodiments of the presently disclosed methods, administering the composition induces an immune response in the subject to at least one tumor-associated and/or cancer-associated antigen present in the composition.

In some embodiments of the presently disclosed methods, the EPELN is derived from a mushroom.

In some embodiments of the presently disclosed methods, the immune response modifier comprises an miRNA, optionally miR18a (5'-UAAGGUGCAUCUAGUGCAGAUAG-3'; SEQ ID NO: 1).

In some embodiments of the presently disclosed methods, the therapeutic agent is selected from a phytochemical agent and a chemotherapeutic agent.

In some embodiments of the presently disclosed methods, the therapeutic agent is a phytochemical agent, and wherein the phytochemical agent is selected from curcumin, resveratrol, baicalein, equol, fisetin, and quercetin.

In some embodiments of the presently disclosed methods, the therapeutic agent is a chemotherapeutic agent selected from the group consisting of retinoic acid, 5-fluorouracil, vincristine, actinomycin D, adriamycin, cisplatin, docetaxel, doxorubicin, and taxol.

In some embodiments of the presently disclosed methods, the therapeutic agent comprises a nucleic acid molecule selected from an siRNA, a microRNA, and a mammalian expression vector.

Thus, it is an object of the presently disclosed subject matter to provide compositions and methods for inducing and/or enhancing anti-tumor and/or anti-cancer immune responses.

An object of the presently disclosed subject matter having been stated herein above, and which is achieved in whole or in part by the presently disclosed subject matter, other objects will become evident as the description proceeds when taken in connection with the accompanying drawings as best described herein below.

BRIEF DESCRIPTIONS OF THE FIGURES

FIG. 1 is schematic depicting an exemplary method for preparing the compositions of the presently disclosed subject matter. TAA1: tumor-associated antigen 1. TAA2: tumor-associated antigen 2.

Figure 2A:
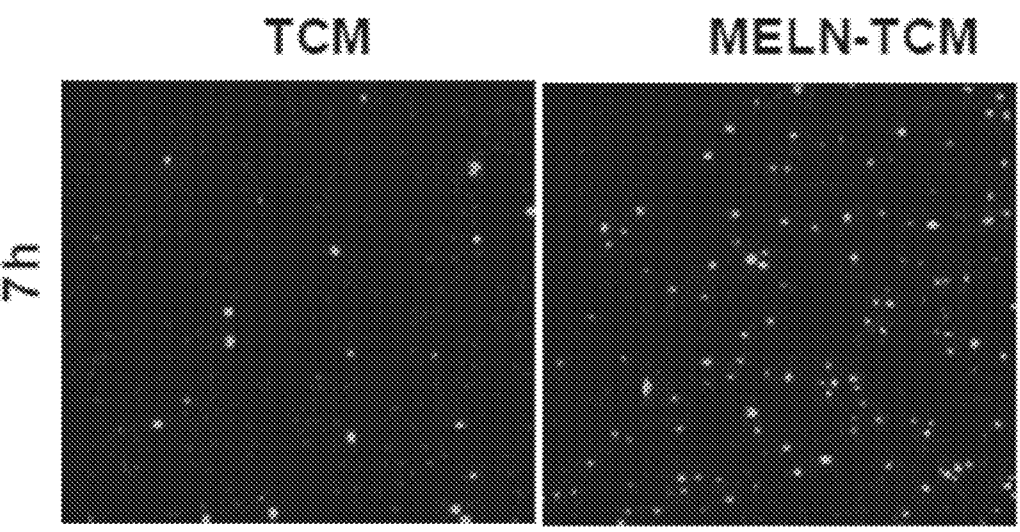
Figure 2B:
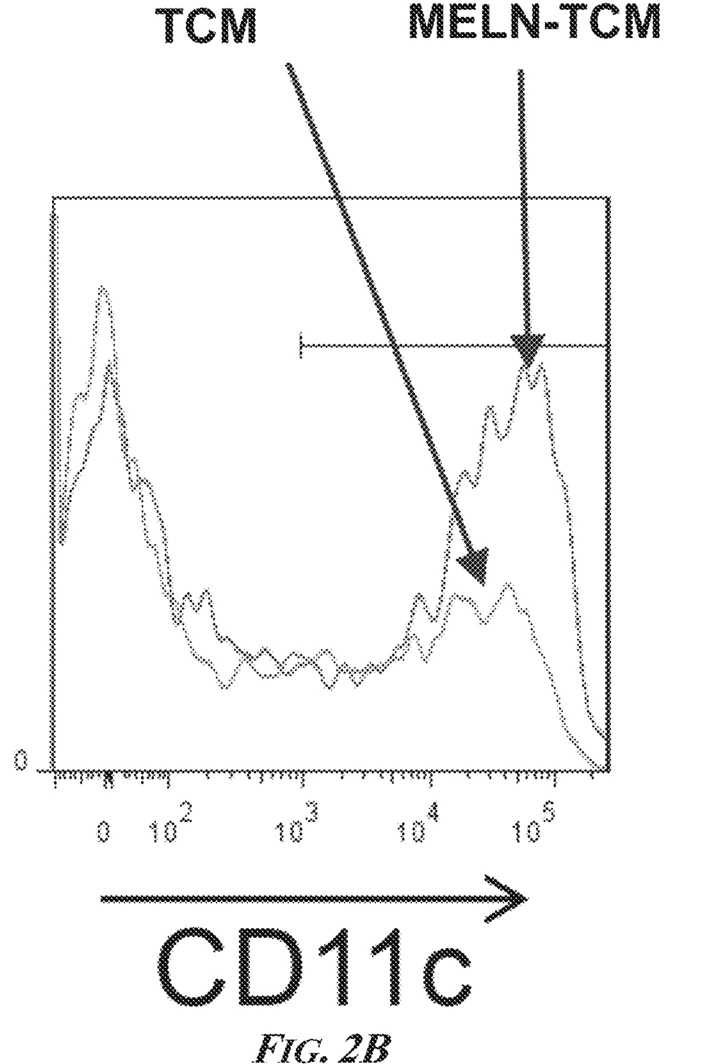
Figure 2C:
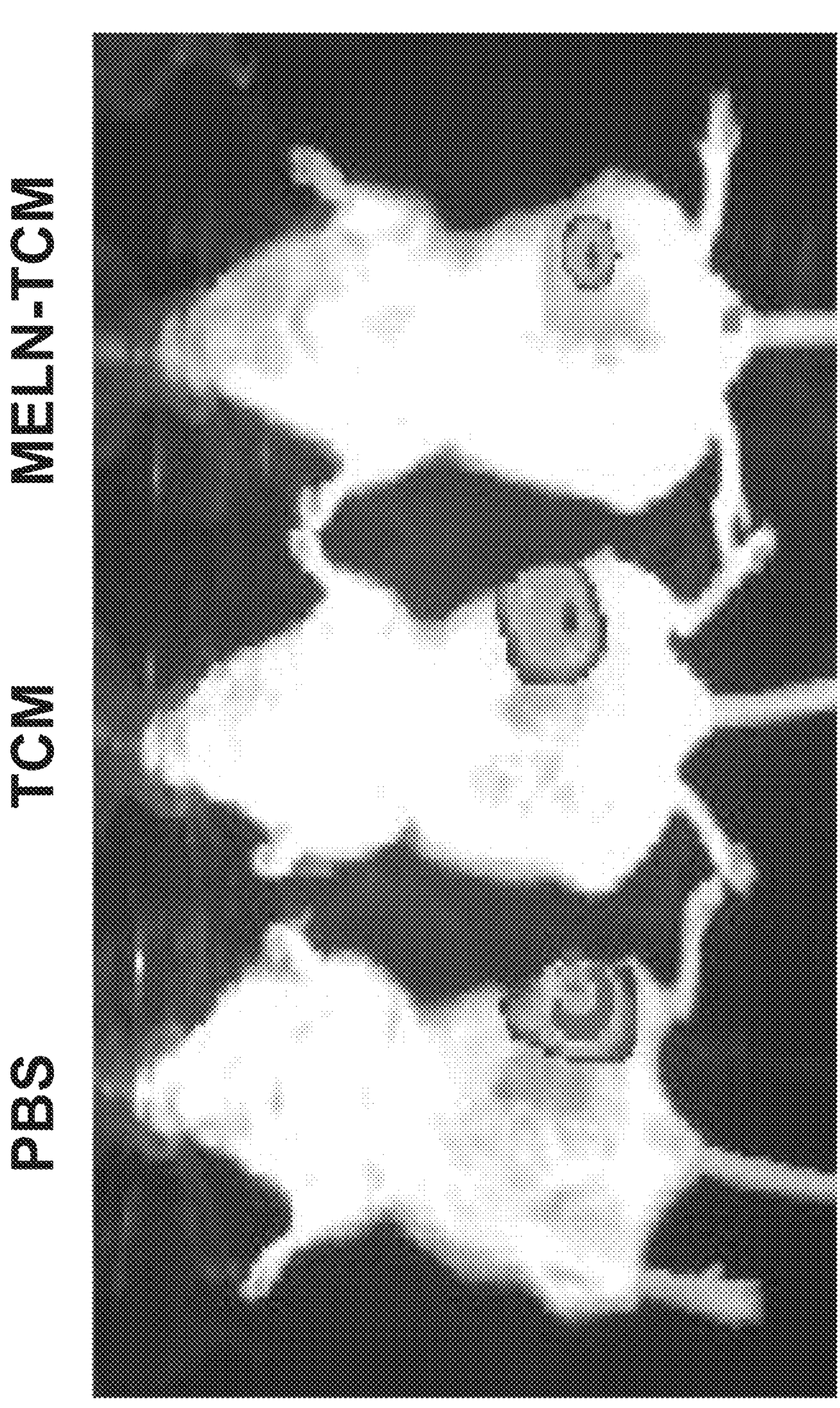

FIGS. 2A-2C show the results of intravenous injection of EPELNs and targeting to CD11c dendritic cells. FIG. 2A is a confocal microscopy image of a phagocytosis assay showing effective uptake of a preparation of tumor cell plasma membranes (TCM) by bone marrow-derived dendritic cells (BMDCs) treated with mushroom-derived exosome-like nanoparticles (MELN). Bone marrow-derived dendritic cells (BMDCs) were pretreated with PBS or MELNs and then cultured with PKH67-labeled TCM (PKH67-TCM) for 7 hours. FIG. 2B is a graph of analysis of the same by flow cytometry. FIG. 2C is a series of images showing the photon emissions of mice subcutaneously injected with $1.0\times10^6$ 4T1-Luc breast tumor cells (4T1 cells that express luciferase) and then intravenously administered PBS, TCM, or MELN-TCM on days 1, 4, and 10 thereafter. The images are at day 30. TCM: tumor cell plasma membrane; MELN: mushroom-derived exosome-like nanoparticles; MELN-TCM: mushroom-derived exosome-like nanoparticles coated with tumor cell plasma membrane (i.e., an exemplary EPELN of the presently disclosed subject matter).

Figures 3A, 3B:
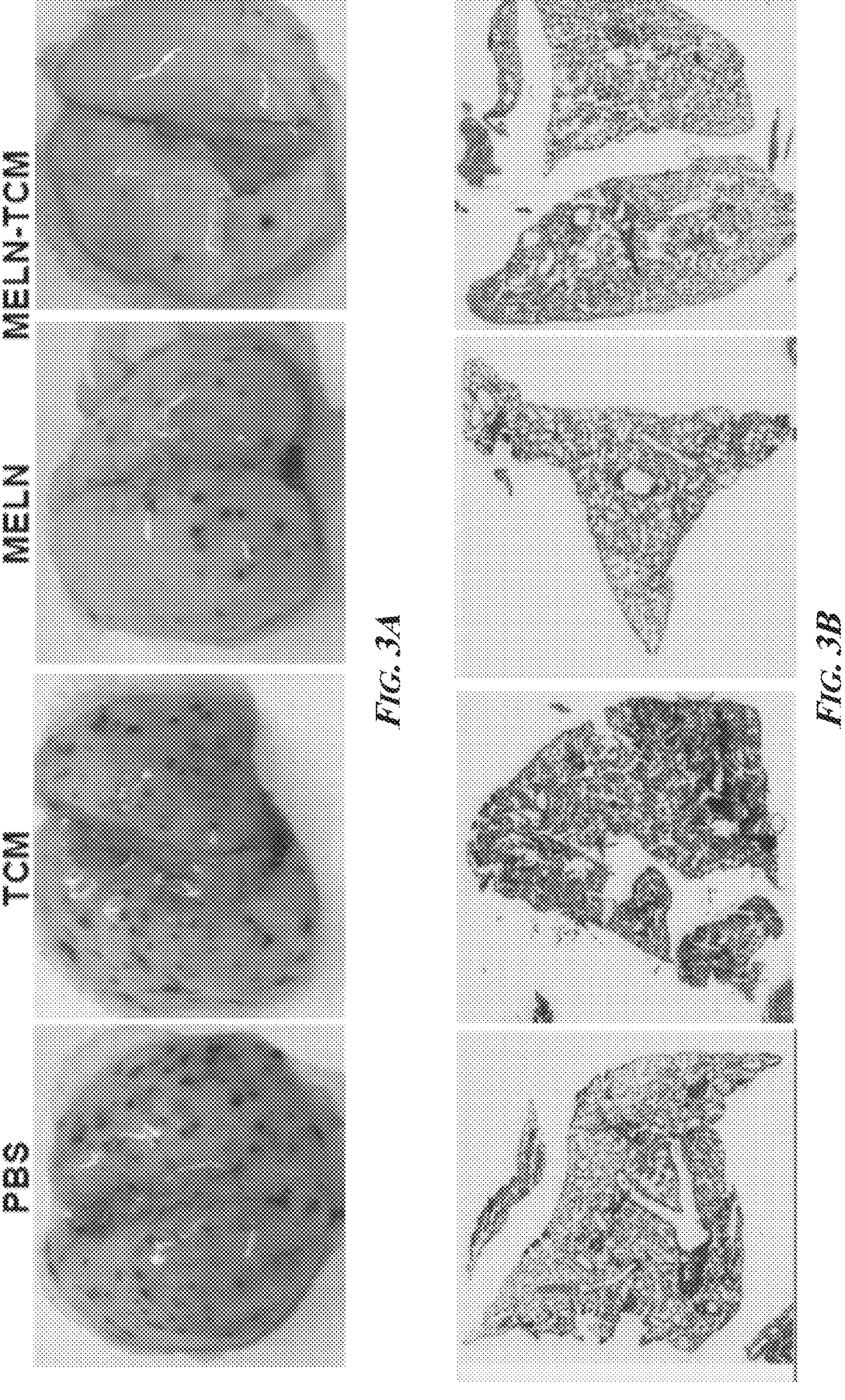
Figure 3C:
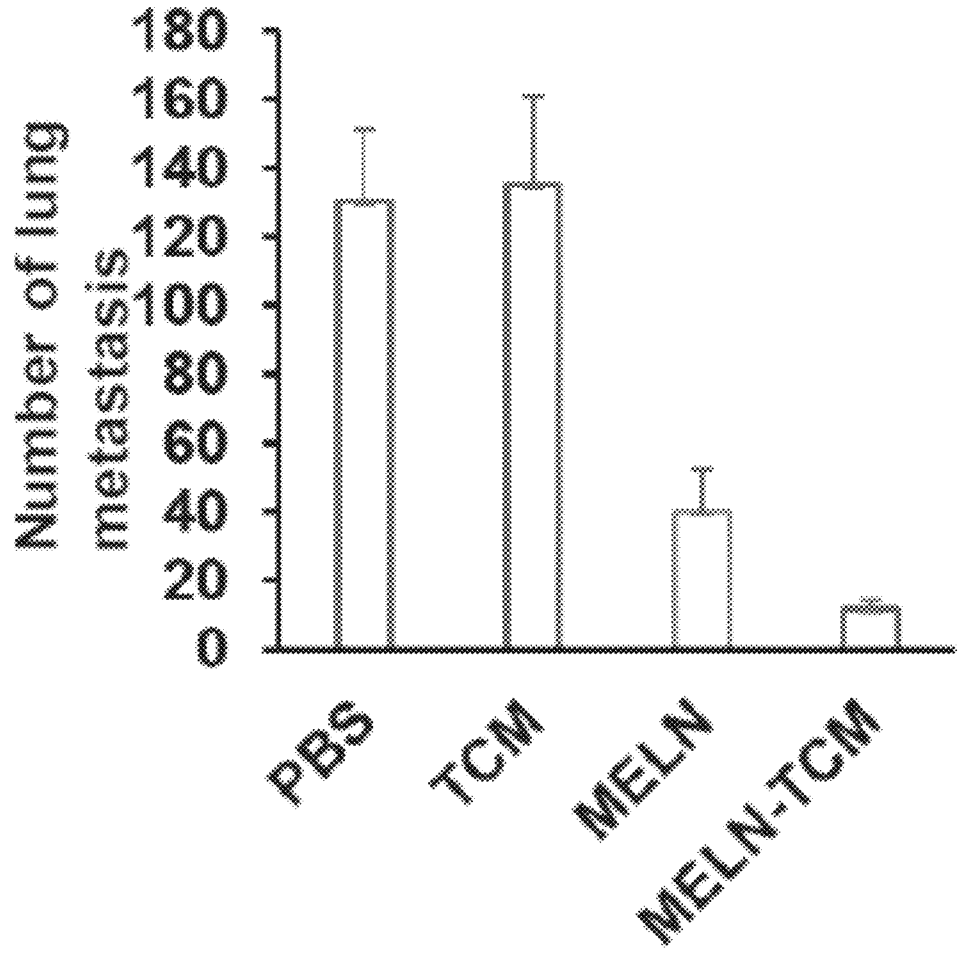

FIGS. 3A-3C show the results of oral administration of EPELNs target to antigen-presenting cells (APCs) and inhibit melanoma lung metastases. FIG. 3A is a series of photographs of isolated lungs from mice that had been intravenously administered $1.0\times10^6$ B16F10 melanoma cells and then administered PBS, TCM, MELN, or MELN+TCM at days 1, 4, 10, and 20 by gavage. The lungs were isolated and photographed at day 30. Lung metastases appear in the Figure as dark black spots. FIG. 3B is a series of H&E-stained sections of lungs shown in FIG. 3A. The darker staining areas correspond to lung metastases. FIG. 3C is a bar graph showing the number of lung metastases at day 30 for each treatment group. Error bars correspond to 1 standard error (SE).

DETAILED DESCRIPTION

Although the use of nanotechnology for the delivery of a wide range of medical treatments has shown potential, the ability to reduce adverse effects associated with drug therapy and ensure tissue-specific delivery remains challenging. As proof of concept, three generations of edible plant exosome-like nanovectors (EPELNs) have been developed with several unique and useful features. First Generation (G1) EPELNs provide in vivo targeting specificity by co-delivering therapeutic agents including chemotherapeutic agents, miRNA, DNA expression vectors, and/or proteins without toxicity (see U.S. Patent Application Publication No. 2012/0315324). Second Generation (G2) EPELNs, which are EPELNs coated with inflammatory-related receptor enriched membranes derived from activated leukocytes (which in some embodiments are derived from grapefruit-derived nanovectors and are referred to herein as inflammatory cell plasma membrane-coated grapefruit-derived nanovectors; IGNVs), were shown to home to inflammatory tissues using three inflammatory-driven disease mouse models (see U.S. Patent Application Publication No. 2017/0035700). The therapeutic potential of inflammatory cell plasma membrane-coated edible plant-derived nanovectors (such as but not limited to IGNVs) was further demonstrated by enhancing the chemotherapeutic effect as shown by inhibition of tumor growth and inhibiting the inflammatory effects of DSS induced mouse colitis.

Disclosed herein are Third Generation (G3) EPELNs, which are edible plant-derived nanovectors that are coated with plasma membranes or fragments or components thereof that are derived from tumor and/or cancer cells. The G3 EPELNs can be employed to elicit immune responses in subjects to specifically kill tumor and/or cancer cells by providing compositions that present tumor-associated and/or cancer-associated antigens to antigen presenting cells (APCs), thereby inducing and/or enhancing immune responses against the tumor-associated and/or cancer-associated antigens in the subjects. As disclosed in more detail herein below.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Furthermore, the terms first, second, third, and the like as used herein are employed for distinguishing between similar elements and not necessarily for describing a sequential or chronological order. It is to be understood that the terms so used are interchangeable under appropriate circumstances and that the subject matter described herein is capable of operation in other sequences than described or illustrated herein.

Following long-standing patent law convention, the articles "a", "an", and "the" refer to "one or more" when used in this application, including in the claims. For example, the phrase "a cell" refers to one or more cells. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the phrase "biological sample" refers to a sample isolated from a subject (e.g., a biopsy) or from a cell or tissue from a subject (e.g., RNA and/or DNA and/or a protein or polypeptide isolated therefrom). Biological samples can be of any biological tissue or fluid or cells from any organism as well as cells cultured in vitro, such as cell lines and tissue culture cells. Frequently the sample will be a "clinical sample" which is a sample derived from a subject (i.e., a subject undergoing or being prepared for a diagnostic procedure and/or a treatment). Typical clinical samples include, but are not limited to cerebrospinal fluid, serum, plasma, blood, saliva, skin, muscle, olfactory tissue, lacrimal fluid, synovial fluid, nail tissue, hair, feces, urine, a tissue or cell type, and combinations thereof, tissue or fine needle biopsy samples, and cells therefrom. Biological samples can also include sections of tissues, such as frozen sections or formalin fixed sections taken for histological purposes. In some embodiments, a biological sample is a biopsy of a tumor and/or a cancer.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter. By way of example and not limitation, a pharmaceutical composition comprising an edible plant-derived exosome-like nanoparticle (EPELN) of the presently disclosed subject matter and a pharmaceutically acceptable carrier, diluent, or excipient can also contain other components including, but not limited to other cells and cell types, other carriers, diluents, and/or excipients, and any other molecule that might be appropriate for inclusion in the pharmaceutical composition without any limitation.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause; other elements are not excluded from the claim as a whole. By way of example and not limitation, a pharmaceutical composition consisting of an EPELN and a pharmaceutically acceptable carrier contains no other components besides the EPELN and the pharmaceutically acceptable carrier. It is understood that any molecule that is below a reasonable level of detection is considered to be absent.

As used herein, the phrase "consisting essentially of" limits the scope of a claim to the specified materials or steps, plus those that do not materially affect the basic and novel characteristic(s) of the claimed subject matter. By way of example and not limitation, a pharmaceutical composition consisting essentially of an EPELN and a pharmaceutically acceptable carrier contains the EPELN and the pharmaceutically acceptable carrier, but can also include any additional elements that might be present but that do not have any biological activity with respect to the desired use of the EPELN.

With respect to the terms "comprising", "consisting essentially of", and "consisting of", where one of these three terms is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

As used herein, the term "isolated" when referring to tumor cells, or cancer cells, and components thereof including but not limited to plasma membranes derived therefrom refers to tumor cells, or cancer cells, and components thereof collected from a subject, in some embodiments a mammalian subject, and in some embodiments a human. Typically, collection of the desired tumor cells, or cancer cells, and components thereof is achieved based on prior identification of the tumor and/or cancer cells as tumor and/or cancer cells, optionally comprising detecting one or more markers that are characteristic of tumor and/or cancer cells, such as but not limited to antibody-based detection and/or radiographic techniques.

As used herein, "optional" or "optionally" means that the subsequently described event or circumstance does or does not occur and that the description includes instances where said event or circumstance occurs and instances where it does not. For example, an optional element of a composition means that in some embodiments the element is present in the composition and in some embodiments, it is not. Similarly, an optional step of a method means that in some embodiments the step is performed in the method and in some embodiments, it is not.

The presently disclosed subject matter generally includes edible plant exosome-like nanovectors (EPELNs). In particular, certain embodiments of the presently disclosed subject matter include EPELNs that include exosome-like nanoparticles (ELPs) coated with plasma membranes and/or fragments or components thereof that are derived from tumor and/or cancer cells.

As used herein, the phrase "edible plant exosome-like nanovectors" refers to exosome-like nanoparticles (ELPs) that can be isolated from edible plants such as by the methods described herein, optionally wherein the ELPs are modified to produce EPELNs. Additional methods for isolating ELPs are described in U.S. Pat. No. 9,717,733 and U.S. Patent Application Publication Nos. 2012/0315324, 2014/0308212, 2017/0035700, 2018/0193266, 2018/0291433, and 2018/0362974, the entire disclosure of each of which is incorporated herein by reference.

With respect to the plasma membrane coating the edible-plant derived microvesicles, the phrase "coating the microvesicle" and variations thereof, is used herein to refer to the covering, placement, and/or attachment of a plasma membrane to the lipid bilayer of an exemplary microvesicle of the presently-disclosed subject matter, or a portion thereof. In some embodiments, the covering of a microvesicle with a plasma membrane derived from a tumor cell and/or a cancer cell is achieved by isolating a tumor and/or a cancer cell such as but not limited to a biopsy comprising tumor and/or cancer cells of interest, lysing and homogenizing the tumor and/or a cancer cell, and collecting the plasma membranes from the tumor and/or a cancer cell by sucrose gradient density centrifugation. After collecting the plasma membranes, the membranes are subsequently sonicated to form vesicles. Such vesicles can then be combined with the exosome-like particles described herein (e.g., microvesicles encapsulating an active agent) and co-extruded through a membrane to thereby coat the microvesicles with the plasma membranes derived from the tumor and/or a cancer cells. In this regard, and without wishing to be bound by any particular, theory, it is believed that by virtue of using plasma membranes derived from activated tumor and/or a cancer cell cells, the resulting microvesicle compositions include a plasma membrane coating having one or more TAAs that are capable of inducing an immune response against the TAAs and thus the tumor and/or cancer cells when presented to an APC.

The presently disclosed subject matter thus relates to exosome-like compositions that include therapeutic agents and are useful in the treatment of various diseases, including tumors and cancers. In some embodiments, the therapeutic agent is encapsulated by an exosome-like particle to thereby provide an exosome-like composition that displays increased in vitro and in vivo solubility, stability, and bioavailability as compared to the free (i.e., non-encapsulated or unbound) therapeutic agent.

As used herein, the phrase "encapsulated by an exosome-like particle", and grammatical variations thereof, is used interchangeably herein with the phrase "exosome-like composition" to refer to edible plant-derived exosome-like particles comprising a lipid bilayer surrounding an active agent (such as but not limited to a therapeutic agent, an immune response modifier, or any combination thereof). By way of example and not limitation, a reference to "exosomal curcumin" refers to an exosome-like particle whose lipid bilayer encapsulates and/or surrounds an effective amount of curcumin.

In some embodiments, the encapsulation of various active (e.g., therapeutic and/or immune response modifying) agents within exosome-like particles can be achieved by first mixing one or more of the therapeutic and/or immune response modifying agents (e.g., phytochemical agents, Stat3 inhibitors, chemotherapeutic agents, miRNAs, etc.)

with isolated exosome-like particles in a suitable buffered solution, such as but not limited to phosphate-buffered saline (PBS). After a period of incubation sufficient to allow the therapeutic and/or immune response modifying agents to become encapsulated during the incubation period, the exosome-like particle/active agent mixture is then subjected to a sucrose gradient (e.g., an 8, 30, 45, and 60% sucrose gradient) to separate the free active agent(s) from the active agent(s) encapsulated within the exosome-like particles followed by a centrifugation step to isolate the exosome-like particles. After this centrifugation step, the exosomal agents are seen as a band in the sucrose gradient such that they can then be collected, washed, and dissolved in a suitable solution for use as described herein.

As noted, in some embodiments, the therapeutic agent is a phytochemical agent. As used herein, the term "phytochemical agent" refers to a non-nutritive plant-derived compound, or an analog thereof. Examples of phytochemical agents include, but are not limited to, compounds such as monophenols; flavonoids, such as flavonols, flavanones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega-3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many cruciferous vegetables.

In some embodiments of the presently disclosed subject matter, the therapeutic agent is a phytochemical agent, which in some embodiments is selected from the group consisting of curcumin resveratrol, baicalein, equol, fisetin, and quercetin. In some embodiments, the phytochemical agent is curcumin. Curcumin is a pleiotropic natural polyphenol with anti-inflammatory, anti-neoplastic, anti-oxidant and chemopreventive activity, with these activities having been identified at both the protein and molecular levels. Nevertheless, limited progress has been reported with respect to the therapeutic use of curcumin as curcumin is insoluble in aqueous solvents and is relatively unstable. In addition, curcumin is known to have a low systemic bioavailability after oral dosing, which further limits its usage and clinical efficacy. It has been determined, however, that by encapsulating curcumin in exosome-like particles, not only can the solubility of curcumin be increased but the encapsulation of the curcumin within the exosome-like particles protects the curcumin from degradation and also increases the bioavailability of the exosomal curcumin.

As also noted herein above, in some embodiments of the presently disclosed subject matter, the active agent that is encapsulated within the exosome-like particle is a chemotherapeutic agent. Examples of chemotherapeutic agents that can be used in accordance with the presently disclosed subject matter include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumoranthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® brand (Bortezomib) proteasome inhibitor (Millennium Pharmaceuticals, Cambridge, Massachusetts, United States of America); or YONDELIS® (trabectedin) brand alkylated agent (Johnson & Johnson, New Brunswick, New Jersey, United States of America). In some embodiments, the chemotherapeutic agent that is encapsulated by an exosome-like particle in accordance with the presently disclosed subject matter is selected from retinoic acid, 5-fluorouracil, vincristine, actinomycin D, adriamycin, cisplatin, docetaxel, doxorubicin, and taxol.

As further noted, in some embodiments, the therapeutic agent is a signal transducer and activator of transcription 3 (Stat3) inhibitor. "Stat3" or "Signal Transducer and Activator of Transcription 3" is a transcription factor encoded by the STAT3 gene and, in response to cytokines or growth factors, is known to become phosphorylated and to then translocate to the nucleus of cells where it mediates the expression of a variety of genes in response to various stimuli, and thus plays a key role in a number of cellular processes including cell growth and apoptosis. In this regard, the term "Stat3 inhibitor" is used herein to refer to any chemical compound or protein that prevents or otherwise reduces the activity of Stat3 including, but not limited to, chemical compounds or proteins that prevent or reduce the transcriptional activity of Stat3, and chemical compounds or proteins that prevent or reduce the activation of Stat3 by preventing its activation (e.g., the phosphorylation and/or translocation of Stat3 to the nucleus of a cell). A number of Stat3 inhibitors are known to those skilled in the art including, but not limited to, the PIAS3 protein, Stattin, or JSI-124, which is also referred to as curcurbitacin I. In some embodiments of the presently disclosed subject matter, the Stat3 inhibitor that is encapsulated within the exosome-like particle is JSI-124.

MicroRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression. There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

In some embodiments, an EPELN of the presently disclosed subject matter encapsulates an miRNA, optionally wherein the miRNA is miR18a or miR17.

The exosome-like particles used to produce the exosome-like compositions of the presently disclosed subject matter can be obtained from a variety of sources using methods known to those of ordinary skill in the art. The term "isolated," when used in the context of an exosome-like particle isolated from a plant, refers to an exosome-like particle that, by the hand of man, exists apart from its native environment and is therefore not a product of nature. For example, in some embodiments, the exosome-like particles are isolated from the juices of plants (e.g., mushrooms). As another example, in some embodiments, the exosome-like particles are isolated from plant cells by collecting plant cell culture supernatants and then purifying the exosome-like particles from the supernatants using known differential centrifugation techniques to isolate exosomes (see e.g., Liu et al. (2006) Murine mammary carcinoma exosomes promote tumor growth by suppression of NK cell function. J Immunol 176(3):1375-1385). As such, in some embodiments, the exosome-like particles that are used in accordance with the presently disclosed subject matter are isolated from a plants and/or plant cells. In some embodiments, the plant cell is a cultured plant cell, that is, a plant cell propagated ex vivo in culture media.

The term "isolated," when used in the context of tumor and/or cancer cell-derived plasma membrane, refers to a plasma membrane or fragment thereof (e.g., a lipid bilayer), or a component thereof, which, by the hand of man, exists apart from its native environment and is therefore not a product of nature. In some embodiments, the tumor and/or cancer cell from which the plasma membrane or fragment thereof is derived (meaning "isolated") is a cultured cell, optionally an immortalized cell line. In some embodiments, the cell is a cancer cell, such as for example a cancer cell originally isolated from a tumor and then propagated in culture, as is generally known in the art. By way of example and not limitation, in some embodiments the cancer cell can be a lymphoma cell, a breast cancer cell, or an adenocarcinoma cell.

Thus, in some embodiments the edible plant exosome-like nanovectors (EPELNs) of the presently disclosed subject matter include exosome-like nanoparticles (ELPs) coated with plasma membranes or fragments or components thereof that are derived from tumor and/or cancer cells. In some embodiments, the tumor and/or cancer cell-derived plasma membranes or fragments or components thereof are employed to coat the entire surface of the ELP, or just a subsurface thereof. It is noted that in some embodiments a function of the EPELNs is to deliver one or more tumor- and/or cancer-associated antigens to APCs in a subject to thereby treat a tumor and/or a cancer in the subject by inducing and/or enhancing an immune response in the subject to the one or more tumor- and/or cancer-associated antigens that are present in the tumor and/or cancer cell-derived plasma membranes or fragments or components thereof.

Therefore, in some embodiments the tumor and/or cancer cell-derived plasma membranes or fragments or components thereof that are employed to coat the ELPs are tumor and/or cancer cell-derived plasma membranes or fragments or components thereof that have been isolated from a tumor and/or cancer biopsy isolated from the subject for whom the treatment is desired. Thus, in some embodiments the tumor and/or cancer cell-derived plasma membranes or fragments or components thereof are autologous to the subject to whom the EPELNs are ultimately administered. It is noted that when a subject is diagnosed with a tumor and/or a cancer, the medical professional typically identifies cells, tissues, and/or organs in the subject that comprise tumor and/or cancer cells. These tumor and/or cancer cells can be isolated from the subject using standard techniques such as but not limited to biopsy, and the biopsied cells can be employed to prepare an anti-tumor and/or anti-cancer vaccine comprising the presently disclosed EPELNs coated with tumor and/or cancer cell-derived plasma membranes or fragments or components thereof as an approach to a personalized anti-tumor and/or anti-cancer treatment for the subject.

Thus, in some embodiments the EPELNs present in the vaccine comprise one or more tumor-associated and/or cancer-associated antigens (collectively referred to herein as "TAAs") as a result of the TAAs being present in the tumor and/or cancer cell-derived plasma membranes or fragments or components thereof employed to produce the EPELNs. As used herein, the phrase "tumor-associated antigen" refers to an antigen which is specifically expressed by tumor cells (also referred to as a "tumor-specific antigen") or expressed at a higher frequency or density by tumor cells than by non-tumor cells of the same tissue type. Tumor-associated antigens can be antigens not normally expressed by the host; they may be mutated, truncated, misfolded, or otherwise abnormal manifestations of molecules normally expressed by the host; they can be identical to molecules normally expressed but expressed at abnormally high levels; or they can be expressed in a context or milieu that is abnormal. Tumor-associated antigens can be, for example, proteins or protein fragments, complex carbohydrates, gangliosides, haptens, nucleic acids, or any combination of these or other biological molecules. Exemplary TAAs are listed in Table 1.

TABLE 1

Exemplary Tumor-associated Antigens

| Gene Name | Associated Tumor or Cancer |
|---|---|
| CEA | Colorectal carcinoma |
| Immature laminin receptor | RCC |
| TAG-72 | Prostate carcinoma |
| HPV E6, E7 | Cervical carcinoma |
| BING-4 | Melanoma |
| Calcium-activated chloride channel 2 | Lung carcinoma |
| Cyclin-B1 | [several] |
| 9D7 | RCC |
| Ep-CAM | Breast carcinoma |
| EphA3 | [several] |
| Her2/neu | [several] |
| Telomerase | [several] |
| Mesothelin | Ductal pancreatic carcinoma |
| SAP-1 | Colorectal carcinoma |
| Survivin | [several] |

TABLE 1-continued

| Exemplary Tumor-associated Antigens | |
|---|---|
| Gene Name | Associated Tumor or Cancer |
| BAGE family | [several] |
| CAGE family | [several] |
| GAGE family | [several] |
| MAGE family | [several] |
| SAGE family | [several] |
| XAGE family | [several] |
| NY-ESO-1/LAGE-1 | [several] |
| PRAME | [several] |
| SSX-2 | Melanoma, [several] |
| Melan-A/MART-1 | Melanoma |
| Gp100/pmel17 | Melanoma |
| Tyrosinase | Melanoma |
| TRP-1/-2 | Melanoma |
| P. polypeptide | Melanoma |
| MC1R | Melanoma |
| Prostate-pecific antigen | Prostate |
| β-catenin | Melanoma, Prostate, HCC |
| BRCA1/2 | Breast, ovarian carcinoma |
| CDK4 | [several] |
| CML66 | CML |
| Fibronectin | [several] |
| MART-2 | Melanoma |
| p53 | [several] |
| Ras | [several] |
| TGF-βRII | Colorectal carcinoma |
| MUC1 | Ductal carcinoma, RCC |
| Ig, TCR | B, T leukemia, lymphoma, myeloma |

An advantage of embodiments of the EPELNs that comprise one or more TAAs for personalized medicine is that the TAAs are also presented to the immune system of the subject (e.g., the subject's APCs) in the context of the Major Histocompatibility (MHC) Antigens already expressed by the subject, such that the anti-TAA immune response induced in the subject is enhanced.

It is noted that in some embodiments the EPELNs of the presently disclosed subject matter comprise one or more TAAs by virtue of the one or more TAAs being present on and/or in the plasma membrane of a tumor and/or a cancer cell that is used to coat the EPELNs. It is noted, however, that TAA polypeptides or peptides derived therefrom (e.g., peptides comprising a subsequence of an TAA, referred to herein as "TAA-derived peptides") can be conjugated directly to an ELN (such as but not limited to an MELN) using standard techniques. In such embodiments, the EPELN is not coated with a plasma membrane that comprises the one or more TAAs but instead is coated with the one or more TAAs or TAA-derived peptides directly.

In some embodiments one or more additional immune response modifiers can be included in the compositions to be administered to a subject. As used herein, the phrase "immune response modifier", and grammatical variants thereof, refers to any molecule that acts to stimulate or otherwise enhance one or more aspects of the immune system of a subject, particularly in the context of enhancing an immune response against and antigen that would not have occurred had the subject not been exposed to the immune response modifier (IRM). Exemplary IRMs are known, such as those disclosed in U.S. Pat. No. 8,557,838; including but not limited to small organic molecule imidazoquinoline amine derivatives (see e.g., U.S. Pat. No. 4,689,338) as well as other compound classes (see e.g., U.S. Pat. Nos. 5,446,153; 6,194,425; and 6,110,929; and PCT International Patent Application Publication No. WO 2005/079195), oligonucleotides including but not limited to CpGs (see e.g., U.S. Pat. No. 6,194,388), and interfering RNAs, in some embodiments microRNAs.

MicroRNAs (miRNAs) are a class of small, non-coding RNAs that post-transcriptionally control the translation and stability of mRNAs. Hundreds of miRNAs are known to have dysregulated expression in cancer. Studies evaluating their biological and molecular roles and their potential therapeutic applications are emerging. The levels of miRNAs expressed in myeloid cells have effects on the polarization of M1 versus M2 macrophages. Targeted delivery of miRNAs to macrophages as an alternative strategy for treatment of cancer by induction of M1 macrophages has not been fully developed.

MiR-18a, an important member of miR-17-92 family, has been shown various effects on different tumors. It was reported that miR-18a could act as a tumor suppressor. miR-18a has been shown to suppress colon tumor growth by targeting β-catenin expressed in the colon tumor cells. It has been discovered that several microRNAs (miRNAs) have IRM activities, including but not limited to miR17 and miR18a. See U.S. Pat. Nos. 8,071,559 and 9,487,781. See also Tsitsiou & Lindsay (2009) MicroRNAs and the Immune Response. Current Opinion in Pharmacology 9:514-520. Thus, in some embodiments an EPELN of the presently disclosed subject matter comprises (in some embodiments encapsulates) an effective amount of an miRNA, optionally wherein the miRNA is selected from the group consisting of miR17 and miR18a.

In some embodiments of the presently disclosed subject matter, the exosome-like compositions of the presently disclosed subject matter specifically bind to a target cell or tissue. Applicants have discovered that exosome-like particles isolated from different plants exhibit tissue- and/or cell-type-specific in vivo tropism, which can advantageously be utilized to direct the exosome-like particles and the exosome-like compositions to a specific cell or tissue. For example, in some embodiments, the exosome-like nanoparticles used to produce an exosome-like composition of the presently disclosed subject matter is derived from a mushroom and specifically binds to APCs including but not limited to CD11c dendritic cells, CD11b4F/80 APCs, or both. While not wishing to be bound by any particular theory of operation, exosome-like nanoparticles (ELNs) derived from mushrooms, including white button mushrooms and Crimini mushrooms, are rich in β-glucans, which are known to have immune response modifier (e.g., adjuvant) activity. As such, while in some embodiments the EPELNs of the presently disclosed subject matter comprise mushroom-derived exosome-like nanoparticles (MELNs), other β-glucan-rich ELNs can also be employed.

In some embodiments of the presently disclosed subject matter, a pharmaceutical composition is provided that comprises an exosome-like composition disclosed herein and a pharmaceutical vehicle, carrier, or excipient. In some embodiments, the pharmaceutical composition is pharmaceutically acceptable for use in humans. Also, as described further below, the pharmaceutical composition can be formulated as a therapeutic composition for delivery to a subject in some embodiments.

A pharmaceutical composition as described herein comprises in some embodiments a composition that includes pharmaceutical carrier, diluent, and/or excipient such as aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in, for example, the following references: U.S. Pat. Nos. 4,839,177; 4,891,223; 5,397,574; 5,399,358; 5,399,359; 5,399,362; 5,419,917; 5,422,123; 5,456,921; 5,458,005; 5,458,887; 5,458,888; 5,464,633; 5,472,708; 5,512,297; 5,603,956; 5,725,883; 5,773,025; 5,824,638; 5,834,023; 5,837,379; 5,885,616; 5,897,876; 5,912,013; 5,916,595; 5,952,004; 6,004,582; 6,077,541; 6,096,340; 6,099,859; 6,099,862; 6,103,263; 6,106,862; and 6,110,498; and PCT International Patent Application Publication No. WO 98/47491, each of which is incorporated herein by this reference in its entirety.

Liquid preparations for oral administration can take the form of, for example, solutions, syrups, or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts and/or flavoring, coloring, and/or sweetening agents as appropriate. Preparations for oral administration can be suitably formulated to give controlled release of the active compound. For buccal administration the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as but not limited to vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the present invention and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the exosome-like compositions of the present invention can also be formulated as rectal compositions, such as suppositories or retention enemas, e.g., containing conventional suppository bases such as cocoa butter or other glycerides. Further, the exosome-like compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

As used herein, the terms "treatment" or "treating" relate to any treatment of a condition of interest (e.g., a tumor or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest (such as but not limited to metastases of a tumor and/or a cancer); reducing the severity of a condition of interest; ameliorating or relieving symptoms associated with a condition of interest; and causing a regression of a condition of interest or one or more of the symptoms associated with a condition of interest.

For administration of a therapeutic composition as disclosed herein (e.g., an EPELN encapsulating a therapeutic agent), conventional methods of extrapolating human dosage based on doses administered to a murine animal model can be carried out using the conversion factor for converting the mouse dosage to human dosage: Dose Human per kg=Dose Mouse per kg×12 (Freireich et al. (1966) Cancer Chemother Rep. 50: 219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. (Freireich et al. (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering a therapeutic composition in accordance with the methods of the presently disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently disclosed subject matter are typically administered in amount effective to achieve the desired response. As such, the term "effective amount" is used herein to refer to an amount of the therapeutic composition (e.g., an EPELN encapsulating a therapeutic agent, and a pharmaceutically vehicle, carrier, or excipient) sufficient to produce a measurable biological response (e.g., inhibit and/or prevent the growth of a tumor cell and/or a cancer cell). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al. (1997) *The Merck Manual of Medical Information, Home ed.* Merck Research Laboratories, Whitehouse Station, New Jersey, United States of America; Goodman et al. (1996) *Goodman & Gilman's The Pharmacological Basis of Therapeutics, 9th ed.* McGraw-Hill Health Professions Division, New York, New York, United States of America; Ebadi (1998) *CRC Desk Reference of Clinical Pharmacology*. CRC Press, Boca Raton, Florida, United States of America.; Katzung (2001) *Basic & Clinical Pharmacology, 8th ed.* Lange Medical Books/McGraw-Hill Medical Pub. Division, New York, New York, United States of America; Remington et al. (1975) *Remington's Pharmaceutical Sciences, 15th ed.* Mack Pub. Co., Easton, Pennsylvania, United States of America.; and Speight et al. (1997) *Avery's Drug Treatment: A Guide to the Properties, Choice, Therapeutic Use and Economic Value of Drugs in Disease Management, 4th ed.* Adis International, Philadelphia, Pennsylvania, United States of America; Duch et al. (1998) Toxicol. Lett. 100-101:255-263.

The skilled artisan will also understand that measuring a reduction in the amount of a certain feature (e.g., tumor and/or cancer cell growth) or an improvement in a certain feature (e.g., the presence of a tumor and/or a cancer) in a subject is a statistical analysis. Statistical significance is often determined by comparing two or more populations, and determining a confidence interval and/or a p value. See e.g., Dowdy & Wearden (1983) *Statistics for Research*, John Wiley & Sons, New York, New York, United States of America, incorporated herein by reference in its entirety. Exemplary confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Thus, in some embodiments, are methods for treating a tumor and/or a cancer. In some embodiments, a method for treating a tumor and/or a cancer is provided that comprises administering to a subject in need thereof an effective amount of an exosome-like composition of the presently disclosed subject matter (i.e., where an exosome-like particle encapsulates a therapeutic agent and optionally wherein the). In some embodiments, the therapeutic agent encapsulated within the exosome-like particle and used to treat the tumor and/or the cancer is selected from a phytochemical agent, a chemotherapeutic agent, and a Stat3 inhibitor as such agents have been found to be particularly useful in the treatment of cancer. The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). As used herein, the terms "cancer and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumorsarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of skin cancer, head and neck cancer, colon cancer, breast cancer, brain cancer, and lung cancer.

As used herein, the term "subject" includes both human and animal subjects. Thus, veterinary therapeutic uses are provided in accordance with the presently disclosed subject matter. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Sambrook et al. (1989) *Molecular Cloning A Laboratory Manual 2nd Ed.*, Cold Spring Harbor Laboratory Press, Cold Spring Harbor, New York, United States of America (Chapters 16 and 17); U.S. Pat. No. 4,683,195; Glover (1985) *DNA Cloning—A Practical Approach, Volumes I and II*; IRL Press, Oxford, Washington, DC, United States of America; Gait (1984) *Oligonucleotide Synthesis—A Practical Approach*, IRL Press, Oxford, Washington, DC, United States of America; Hames & Higgins (1985) *Nucleic Acid Hybridisation: A Practical Approach*, IRL Press, Oxford, Washington, DC, United States of America; Hames & Higgins (1984) *Transcription and Translation: A Practical Approach*, IRL Press, Oxford, Washington, DC, United States of America; Freshney (2016) *Culture of Animal Cells: A Manual of Basic Technique and Specialized Applications*, John Wiley & Sons, Hoboken, New Jersey, United States of America; Woodward (1985) *Immobilised Cells and Enzymes: A Practical Approach*, IRL Press, Oxford, Washington, DC, United States of America; Perbal (1984), *A Practical Guide to Molecular Cloning*, John Wiley & Sons, Hoboken, New York, United States of America; Miller & Calos (1987) *Gene Transfer Vectors for Mammalian Cells*, Cold Spring Harbor Laboratory Press, Cold Spring Harbor, New York, United States of America; Wu & Grossman (1987) *Methods in Enzymology, Volumes* 154 (*Recombinant DNA Part E*) *and* 155 (*Recombinant DNA Part F*). Academic Press Inc., New York, United States of America; Mayer & Walker (1987) *Immunochemical Methods in Cell and Molecular Biology*. Academic Press, London, United Kingdom; Herzenberg et al. (1996) *Weir's Handbook of Experimental Immunology* (*Four-Volume Set*) *5th Ed*., Wiley-Blackwell, Hoboken, New Jersey, United States of America.

In some embodiments, a composition is provided that comprises an edible-plant derived exosome-like nanoparticle coated with a plasma membrane derived from a tumor cell. In some embodiments, the tumor cell is obtained from a subject. In some embodiments, the composition further comprises one or more miRNAs. In some embodiments, the edible plants are a mushroom such that, in certain embodiments, the term "edible plant" is inclusive of edible mushrooms.

Further provided, in some embodiments of the presently disclosed subject matter are methods for treating a cancer. In some embodiments, a method of treating a cancer is provided that comprises administering to a subject in need thereof a composition comprising an edible-plant derived exosome-like nanoparticle coated with a plasma membrane derived from a tumor cell. In some embodiments, the composition is administered orally or intravenously.

In some embodiments of the therapeutic methods described herein, antigen presenting cells (APCs) can be targeted effectively in vivo by intravenously or orally administering the mushroom derived exosomes-like nanoparticles (MELNs) coated with multiple tumor antigens from tumor cells or tumor tissue from individual cancer patients. Consequently, in such embodiments, strong T-cell responses against both tumor growth and metastasis can be induced. Therefore, in certain embodiments, MELNs represent a universally applicable delivery vehicle for targeted delivery of agents for personalized therapy.

In some embodiments, the compositions described herein can be used as an oral cancer vaccine for protection against tumor development, which, in some embodiments, is beneficial in families who are susceptible to cancer development. In some embodiments, the compositions can be administered subcutaneously for the treatment of an infectious disease, such as a mutant bacteria that is resistant to antibiotic treatment or such as parasite or fungal infection that is currently untreatable by a specific vaccine or drug.

Thus, in some embodiments the presently disclosed subject matter relates to methods for using the presently disclosed compositions for various purposes including but not limited to the following:

In some embodiments, the methods relate to treating tumors and/or cancers by administering to a subject in need thereof an effective amount of a composition, wherein the composition comprises an edible-plant derived exosome-like nanoparticle (EPELN) encapsulating and/or having associated therewith an active agent selected from the group consisting of a therapeutic agent and an immune response modifier; and a plasma membrane derived from a tumor and/or cancer cell coating the EPELN, wherein the plasma membrane comprises one or more tumor-associated and/or cancer-associated antigens.

In some embodiments, the methods relate to treating a tumor and/or a cancer in a subject by providing an edible-plant derived exosome-like nanoparticle (EPELN) encapsulating and/or having associated therewith an active agent selected from the group consisting of a therapeutic agent and an immune response modifier; coating the EPELN with a plasma membrane derived from a tumor and/or a cancer cell isolated from the subject to produce a therapeutic composition; and administering an effective amount of the therapeutic composition to the subject, whereby the therapeutic composition induces an immune response in the subject against a tumor-associated and/or cancer-associated antigen to thereby treat the tumor and/or the cancer in the subject.

In some embodiments, the methods relate to inducing an anti-tumor and/or an anti-cancer immune response in a subject, the method comprising administering to the subject an effective amount of a presently disclosed composition, whereby an anti-tumor and/or anti-cancer immune response is induced in the subject to at least one tumor-associated and/or cancer-associated antigen present in the composition.

In some embodiments, the methods relate to activating antigen-presenting cells (APCs) in a subject, the method by administering to the subject an effective amount of a presently disclosed composition, whereby APCs present in the subject are activated against at least one tumor-associated and/or cancer-associated antigen present in the subject.

In some embodiments, the methods relate to targeting a CD11c dendritic cell present in or isolated from a subject by contacting the CD11c dendritic cell with a composition as disclosed herein.

In some embodiments, the methods relate to preventing or reducing metastasis of a cancer in a subject in need thereof by administering to the subject an effective amount of a composition as disclosed herein.

In some embodiments, the methods relate to activating an antigen-presenting cell (APC) in a subject against a tumor cell and/or a cancer cell. In some embodiments, the methods comprise administering to the subject an effective amount of a composition comprising an edible-plant derived exosome-like nanoparticle (EPELN) encapsulating and/or having associated therewith an active agent selected from the group consisting of a therapeutic agent and an immune response modifier; and a plasma membrane derived from a tumor and/or cancer cell coating the EPELN, wherein the plasma membrane comprises one or more tumor-associated and/or cancer-associated antigens, whereby an antigen-presenting cell (APC) in a subject is activated against the tumor cell and/or the cancer cell.

In some embodiments of the presently disclosed subject matter, the EPELN comprises a plasma membrane, or a fragment or component thereof, that is derived from and/or isolated from tumor cell and/or a cancer cell that is autologous to the subject to which it is administered.

In some embodiments of the presently disclosed subject matter, the EPELN-containing composition is administered orally or intravenously to a subject.

In some embodiments of the presently disclosed subject matter, administering the EPELN-containing composition induces an immune response in the subject to at least one tumor-associated and/or cancer-associated antigen present in the EPELN-containing composition.

In some embodiments of the presently disclosed subject matter, the EPELN comprises an exosome-like particle that is derived from a mushroom. A mushroom is the fleshy, spore-bearing fruiting body of a fungus, and mushroom-derived EPLENs are likely to have additional immunostimulating roles when taken by APCs, thereby leading to more matured APCs for better activation of anti-tumor cytotoxic T cells.

In some embodiments of the presently disclosed subject matter, the EPELN comprises, optionally encapsulates, an immune response modifier (IRM), wherein in some embodiments the IRM comprises an miRNA, optionally miR18a (5'-UAAGGUGCAUCUAGUGCAGAUAG-3'; SEQ ID NO: 1).

In some embodiments of the presently disclosed subject matter, the EPELN comprises, optionally encapsulates, a therapeutic agent, optionally wherein the therapeutic agent is selected from a phytochemical agent and a chemotherapeutic agent. In some embodiments, the therapeutic agent is a phytochemical agent, wherein the phytochemical agent is optionally selected from curcumin, resveratrol, baicalein, equol, fisetin, and quercetin. In some embodiments, the therapeutic agent is a chemotherapeutic agent, optionally a chemotherapeutic agent selected from the group consisting of retinoic acid, 5-fluorouracil, vincristine, actinomycin D, adriamycin, cisplatin, docetaxel, doxorubicin, and taxol. In some embodiments, the therapeutic agent comprises an interfering nucleic acid molecule, optionally selected from an siRNA, a microRNA, and a mammalian expression vector.

EXAMPLES

The presently disclosed subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Materials and Methods for the EXAMPLES miRNAs: miR18a has the sequence 5'-UAAGGUG-CAUCUAGUGCAGAUAG-3' (SEQ ID NO: 1), and this sequence was used unlabeled as disclosed herein.

Animals: 7- to 10-week female BALB/c mice (The Jackson Laboratory, Bar Harbor, Me.) were used. All animal studies were conducted within the guidelines established by an Institutional Animal Care and Use Committee.

Preparation of EPELNs: MELNs were purified by sucrose gradient as essentially described in U.S. Patent Application Publication No. 2017/0035700. Briefly, white button mushrooms or Crimini mushrooms were purchased from a local market, washed, and sterilized under a UV lamp for 30 minutes, and processed using Good Laboratory Practice (GLP) procedures. The mushrooms were cut into several pieces, and the fluids collected into centrifuge tubes for purification of ELNs using gradient centrifugation. The skin of the mushrooms was removed by centrifugation for 10 minutes at 200×g. Supernatants were collected and centrifuged sequentially twice for 10 minutes at 500×$g_{max}$, once for 15 minutes at 2,000×$g_{max}$, and once for 30 minutes at 10,000×$g_{max}$. The pellet was referred to as microparticles. The supernatants were mixed with endogenous exosome-depleted skim milk (1:1 by volume) and centrifuged for 60 minutes at 100,000×$g_{max}$. The pellet was collected, resuspended, and the exosome-like particles were collected by sucrose gradient centrifugation. Exosome-like particles were then washed with endogenous exosome-depleted skim milk once and then resuspended in PBS. Purity and integrity of sucrose gradient-isolated MELNs was analyzed using a Hitachi H7000 electron microscope (Electronic Instruments, Akishima, Japan)

Purified EPELNs were harvested from the 30%/45% interface. The lipids were extracted with chloroform and dried under vacuum. The concentration of lipids was measured using the phosphate assay.

Phosphate quantification: Phosphate was quantified using a standard Phosphorus solution (0.65 mM, P3869-25 ml from Sigma-Aldrich Corp., St. Louis, Missouri, United States of America). First, different amounts of phosphate standard solutions (50, 25, 10, 5 and 0 nmol) were prepared in 100 μl ddH2O, then 30 μl $Mg(NO_3)_2$ was added, and the mixture was heated by flame until dry. The dried sample was dissolved in 300 μl HCl and heated at 100° C. for 15 minutes, cooled, and centrifuged at 1000 rpm for 2 minutes. 700 μl of the reaction buffer (1 part of 10% ascorbic acid and 6 parts 0.42% ammonium molybdate in 1 N $H_2SO_4$) were added and mixture incubated at 45° C. for 20 minutes. The absorption was read at $OD_{280}$.

Preparation of EPELNs encapsulating miRNA18a: To generate EPELNs or MELNs carrying miR18a as an example, 200 nmol of lipid was suspended in 200-400 μl of 155 mM NaCl with 10 μg of RNA. After UV irradiation at 500 mJ/cm2 in a Spectrolinker (Spectronic Corp.) and bath sonication (FS60 bath sonicator; Fisher Scientific) for 30 minutes, the pelleted particles were collected by centrifugation at 100,000 g for 1 hour at 4° C. The size and zeta potential distribution of the particles was analyzed using a Zetasizer Nano ZS (Malvern Instrument, United Kingdom).

Example 1

Preparation of Tumor Cell Membrane-Coated MELNs (MELN-TCM)

Mouse tumor cell line 4T1 cells or B16F10 cells were collected and centrifuged at 500 g for 10 minutes at 4° C. The cell pellets were resuspended in 1 ml of homogenization buffer at a final concentration of 10 mM in Tris-HCL, 25 mM D-sucrose, 1 mM $MgCl_2$, 1 mM KCL, 10 μg/ml RNase, 10 μg/ml DNase, and 1× proteinase inhibitor cocktail. The cell suspension was homogenized on ice by 100 passes using a hand-held Dounce homogenizer. The supernatant was collected after centrifugation at 500 g for 10 minutes. For further purification, collected supernatants were subjected to a discontinuous sucrose density gradient centrifugation at 28,000 g for 45 minutes at 4° C. on a 30%, 40% and 55% sucrose gradient in a 0.9% saline solution.

The plasma membranes purified from tumor cells were then sonicated in a glass vial with 200 μl ddH2O for 10 minutes using a FS30D bath sonicator (Fisher Scientific). The resulting vesicles were subsequently extruded through 100 nm polycarbonate porous membranes using an Avanti mini extruder (Avanti Polar Lipids).

To prepare the tumor cell membrane-coated MELNs (MELN-TCM), 400 nmol of MELN were mixed with 4T1 cell-derived or B16F10 cell-derived TCM and extruded 20 times through a 200 nm polycarbonate porous membrane using an Avanti mini extruder to form the appropriate MELN-TCM depending on which tumor cell type was to be tested.

This general procedure is outlined in FIG. 1, which also includes the approach to encapsulating an IRM such as but not limited to niR18a prior to coating the MELN with the TCM.

Example 2

Update of EPELNs by CD11c APCs

TCM and MELN-TCM were prepared as described. Bone marrow-derived dendritic cells (BMDCs) were pretreated with PBS or MELNs and then cultured with PKH67-labeled TCM (PKH67-TCM) for 7 hours. A phagocytosis assay was employed to test the uptake of TCM and MELN-TCM by BMDCs. Confocal microscopy (FIG. 2A) and flow cytometry (FIG. 2B) were used to analyze the uptake of PKH67-labeled TCM by BMDCs. FIGS. 2A and 2B show that the MELN-TCM EPELNs were taken up by BMDCs to a greater degree than was TCM alone.

Example 3

Intravenously Administered EPELNs Target to CD11c Dendritic Cells to Inhibit Growth of Breast Tumor Cells Mice were implanted with $1.0\times10^6$ 4T1-Luc cells subcutaneously in the left flank on day 0. On days 1, 4, and 10, Mushroom-derived EPELNs encapsulating miR18a were administered intravenously.

cells to the lungs. Metastases are seen as black spots on the lungs in FIG. 3A. Sections of the isolated lungs were also prepared and stained with Hematoxylin and Eosin (H&E) and representative examples are shown in FIG. 3B. The darker staining sections correspond to metastases, and were particularly observed in the negative control (PBS) and TCM-treated lungs. FIG. 3C provides a bar graph quantitating the number of lung metastases identified in each treatment group, with the MELN-treatetd and MELN+TCM-treated lungs showing large reductions in lung metastases as compared to the negative control and TCM-treated lungs.

REFERENCES

All references listed in the instant disclosure, including but not limited to all patents, patent applications and publications thereof, scientific journal articles, and database entries (including but not limited to GENBANK® biosequence database entries and all annotations available therein) are incorporated herein by reference in their entireties to the extent that they supplement, explain, provide a background for, or teach methodology, techniques, and/or compositions employed herein.

It will be understood that various details of the presently disclosed subject matter can be changed without departing from the scope of the subject matter disclosed herein. Furthermore, the foregoing description is for the purpose of illustration only, and not for the purpose of limitation.

SEQUENCE LISTING

```
Sequence total quantity: 2
SEQ ID NO: 1            moltype = RNA  length = 23
FEATURE                 Location/Qualifiers
source                  1..23
                        mol_type = other RNA
                        organism = Homo sapiens
SEQUENCE: 1
taaggtgcat ctagtgcaga tag                                          23

SEQ ID NO: 2            moltype = RNA  length = 23
FEATURE                 Location/Qualifiers
source                  1..23
                        mol_type = other RNA
                        organism = Homo sapiens
SEQUENCE: 2
caaagtgctt acagtgcagg tag                                          23
```

On day 30, the mice were imaged to determine the extent to which TCM and MELN-TCM inhibited growth of the introduced tumor cells. As can be seen in FIG. 2C, TCM inhibited growth of the 4T1-Luc cells, but MELN-TCM did so to a considerably greater extent.

Example 4

EPELNs Target to Antigen-Presenting Cells to Inhibit Lung Metastasis of Melanoma Cells Mice were administered $1.0\times10^6$ B16F10 melanoma cells by i.v. injection on day 0. On days 1, 4, 10, and 20, EPELNs encapsulating miR18a were administered by gavage. On day 30, the mice were sacrificed, and lungs were isolated and photographed. The results are presented in FIG. 3A.

As shown in FIG. 3A, TCM, MELN, and MELN+TCM treatment inhibited metastasis of the introduced melanoma

What is claimed is:

1. A composition comprising:

an edible-plant derived exosome-like nanoparticle (EPELN) comprising a lipid bilayer encapsulating and/or having associated therewith an immune response modifier; wherein the immune response modifier comprises an miRNA selected from the group consisting of miR18a (5'-UAAGGUGCAUCUAGUGCAGAUAG-3'; SEQ ID NO: 1) and miR17 (5'-CAAAGUGCUUACAGUGCAGGUAG-3'; SEQ ID NO: 2); and a plasma membrane; wherein the plasma membrane is derived from a tumor and/or cancer cell and wherein the plasma membrane consists of one or more tumor-associated antigens and/or cancer associated antigens.

2. The composition of claim 1, wherein the edible plant is a mushroom.

3. The composition of claim 1, wherein the (EPELN) further encapsulates and/or has associated therewith a therapeutic agent.

4. The composition of claim 3, wherein the therapeutic agent is selected from a phytochemical agent, an immune response inducing and/or enhancing agent, and a chemotherapeutic agent.

5. The composition of claim 3, wherein the therapeutic agent is a phytochemical agent, optionally wherein the phytochemical agent is selected from curcumin, resveratrol, baicalein, equal, fisetin, and quercetin.

6. The composition of claim 3, wherein the therapeutic agent is a chemotherapeutic agent, optionally wherein the chemotherapeutic agent is selected from the group consisting of retinoic acid, 5-fluorouracil, vincristine, actinomycin D, adriamycin, cisplatin, docetaxel, doxorubicin, and taxol.

7. The composition of claim 3, wherein the therapeutic agent comprises a nucleic acid molecule selected from the group consisting of an siRNA, a microRNA, and a mammalian expression vector.

8. A pharmaceutical composition comprising a pharmaceutically-acceptable vehicle, carrier, and/or excipient and the composition of claim 1, optionally wherein the pharmaceutical composition is pharmaceutically acceptable for use in a human.

9. A method for treating a tumor and/or a cancer, the method comprising administering to a subject in need thereof an effective amount of a composition, the composition comprising:

(i) an edible-plant derived exosome-like nanoparticle (EPELN) comprising a lipid bilayer encapsulating and/or having associated therewith an immune response modifier; wherein the immune modifier comprises an miRNA selected from the group consisting of miR18a (5'-UAAGGUGCAUCUAGUGCAGAUAG-3'; SEQ ID NO: 1) and miR17 (5'-CAAAGUGCUUACAGUGCAGGUAG-3'; SEQ ID NO: 2); and (ii) a plasma membrane derived from a tumor and/or cancer cell coating the EPELN; and wherein the plasma membrane consists of one or more tumor-associated antigens and/or cancer associated antigens.

10. The method of claim 9, wherein the tumor cell and/or cancer cell is autologous to the subject.

11. A method for inducing an anti-tumor and/or an anti-cancer immune response in a subject, the method comprising administering to the subject an effective amount of the composition of claim 1, whereby an anti-tumor and/or anti-cancer immune response is induced in the subject to at least one tumor-associated and/or cancer-associated antigen present in the composition.

12. A method for activating antigen-presenting cells (APCs) in a subject, the method comprising administering to the subject an effective amount of the composition of claim 1, whereby APCs present in the subject are activated against at least one tumor-associated and/or cancer associated antigen present in the subject.

13. A method for targeting a CD11c dendritic cell present in or isolated from a subject, the method comprising contacting the CD11c dendritic cell with a composition of claim 1.

14. A method for inhibiting or reducing metastasis of a cancer in a subject in need thereof, the method comprising administering to the subject an effective amount of a composition of claim 1.

15. The method of claim 9, wherein the composition is administered orally or intravenously.

16. The method of claim 9, wherein administering the composition induces an immune response in the subject to at least one tumor-associated and/or cancer-associated antigen present in the composition.

17. The method of claim 9, wherein the EPELN is derived from a mushroom.

18. The method of claim 9, wherein the immune response modifier comprises miR 18a (5'UAAGGUGCAUCUAGUGCAGAUAG-3'; SEQ ID NO: 1).

19. The method of claim 9, wherein the (EPELN) further encapsulates and/or has associated therewith a therapeutic agent.

20. The method of claim 19, wherein the therapeutic agent is selected from a phytochemical agent and a chemotherapeutic agent, optionally wherein the therapeutic agent comprises:

(i) a phytochemical agent selected from curcumin, resveratrol, baicalein, equal, fisetin, and quercetin; or (ii) a chemotherapeutic agent selected from the group consisting of retinoic acid, 5-fluorouracil, vincristine, actinomycin D, adriamycin, cisplatin, docetaxel, doxorubicin, and taxol: or (iii) a nucleic acid molecule selected from an siRNA a microRNA and a mammalian expression vector.

21. The composition of claim 1, wherein the wherein the immune response modifier comprises miR17 (5'-CAAAGUGCUUACAGUGCAGGUAG-3'; SEQ ID NO: 2).

22. The composition of claim 9, wherein the wherein the immune response modifier comprises miR17 (5'-CAAAGUGCUUACAGUGCAGGUAG-3'; SEQ ID NO: 2).

* * * * *